United States Patent
Weiguny et al.

(10) Patent No.: US 7,157,403 B2
(45) Date of Patent: Jan. 2, 2007

(54) CATALYST-PRECURSOR FOR THE PRODUCTION OF MALEIC ACID ANHYDRIDE AND METHOD FOR THE PRODUCTION THEREOF

(75) Inventors: Jens Weiguny, Shanghai (CN); Sebastian Storck, Mannheim (DE); Mark Duda, Ludwigshafen (DE); Cornelia Dobner, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 175 days.

(21) Appl. No.: 10/507,609

(22) PCT Filed: Mar. 12, 2003

(86) PCT No.: PCT/EP03/02509

§ 371 (c)(1),
(2), (4) Date: Sep. 14, 2004

(87) PCT Pub. No.: WO03/078059

PCT Pub. Date: Sep. 25, 2003

(65) Prior Publication Data

US 2005/0222435 A1    Oct. 6, 2005

(30) Foreign Application Priority Data

Mar. 15, 2002    (DE)    ................ 102 11 449

(51) Int. Cl.
*B01J 27/198*    (2006.01)
*C07D 307/60*    (2006.01)

(52) U.S. Cl. ....................... 502/209; 549/259
(58) Field of Classification Search ........... 549/259; 502/209
See application file for complete search history.

(56) References Cited

U.S. PATENT DOCUMENTS

| 4,064,070 A | 12/1977 | Harrison |
| 4,132,670 A | 1/1979 | Katsumoto et al. |
| 4,147,661 A | 4/1979 | Higgins et al. |
| 4,333,853 A | 6/1982 | Milberger et al. |
| 4,668,652 A | 5/1987 | Fumagalli et al. |
| 5,275,996 A | 1/1994 | Andrews et al. |
| 5,922,637 A | 7/1999 | Bortinger |

FOREIGN PATENT DOCUMENTS

| EP | 31 696 | 7/1981 |
| EP | 56 183 | 7/1982 |
| EP | 151 912 | 8/1985 |
| EP | 221 876 | 5/1987 |
| EP | 799 795 | 10/1997 |
| EP | 804 963 | 11/1997 |
| WO | 9/04269 | 3/1994 |
| WO | 95/26817 | 10/1995 |

OTHER PUBLICATIONS

Ullmann's Encyclopedia of Industrial Chemistry, 6th Ed., 2000, Electron release, Chapter "Maleic and Fumaric Acids, Maleic Anhydride- Production".

*Primary Examiner*—Bernard Dentz
(74) *Attorney, Agent, or Firm*—Novak Druce & Quigg LLP (57) ABSTRACT

A process for preparing a vanadium, phosphorus, and oxygen catalyst precursor for preparing maleic anhydride by heterogeneously catalyzed gas-phase oxidation of a hydrocarbon having at least four carbon atoms, by reacting vanadium pentoxide (I) in the presence of a primary or secondary, noncyclic or cyclic, unbranched or branched, saturated alcohol having from 3 to 6 carbon atoms (II) with a pentavalent or trivalent phosphorus compound (III) in a temperature range from 80 to 160° C. with stirring and subsequently filtering the resultant suspension, in which (a) the way in which the phosphorus compound (III) and the vanadium pentoxide (I) are combined in the presence of the alcohol (II), (b) the action of a stirring power of from 0.01 to 0.6 W/kg suspension, and/or (c) the filtration at a temperature from 65° C. to 160° C. are used to set a filtration resistance $\alpha_H \cdot \eta$ of $<50 \cdot 10^{13}$ mPa·s/m²; a catalyst precursor obtainable from this process; a process for preparing a catalyst from the catalyst precursor; a catalyst obtainable from this process; and a process for preparing maleic anhydride over this catalyst.

10 Claims, 1 Drawing Sheet

Figure 1:
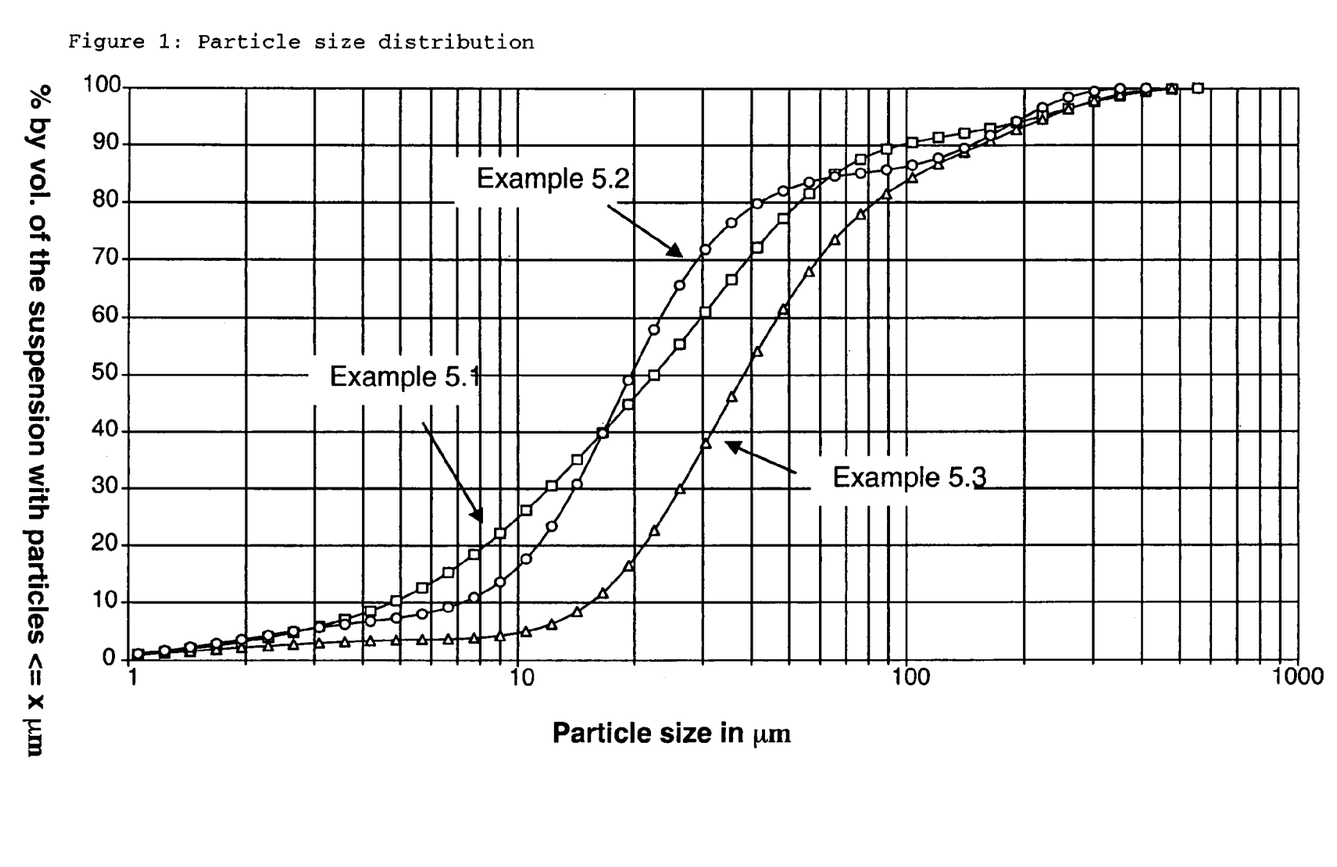

Figure 1: Particle size distribution

CATALYST-PRECURSOR FOR THE PRODUCTION OF MALEIC ACID ANHYDRIDE AND METHOD FOR THE PRODUCTION THEREOF

This application is a 371 of PCT/EP03/02509 filed Mar. 12, 2003.

The present invention relates to a process for preparing a vanadium, phosphorus, and oxygen catalyst precursor for preparing maleic anhydride by heterogeneously catalyzed gas-phase oxidation of a hydrocarbon having at least four carbon atoms, by reacting vanadium pentoxide (I) in the presence of a primary or secondary, noncyclic or cyclic, unbranched or branched, saturated alcohol having from 3 to 6 carbon atoms (II) with a pentavalent or trivalent phosphorus compound (III) in a temperature range from 80 to 160° C. with stirring and subsequently filtering the resultant suspension, and to a catalyst precursor prepared by this process.

The present invention further relates to a vanadium-phosphorus-oxygen catalyst and to a process for preparing it using the catalyst precursor of the invention.

The present invention additionally relates to a process for preparing maleic anhydride by heterogeneously catalyzed gas-phase oxidation of a hydrocarbon having at least four carbon atoms, using the catalyst of the invention.

Maleic anhydride is an important intermediate in the synthesis of γ-butyrolactone, tetrahydrofuran, and 1,4-butanediol, which in their turn are used as solvents or are further processed, for example, to polymers, such as polytetrahydrofuran or polyvinylpyrrolidone.

The preparation of maleic anhydride by oxidizing hydrocarbons such as n-butane, n-butenes or benzene over suitable catalysts is well established. It is generally carried out using vanadium-phosphorus-oxygen catalysts (known as VPO catalysts) (see Ullmann's Encyclopedia of Industrial Chemistry, $6^{th}$ edition, 2000 electronic release, Chapter "MALEIC AND FUMARIC ACIDS, Maleic Anhydride—Production").

The VPO catalysts generally employed are normally prepared as follows:

(1) synthesis of a vanadyl phosphate hemihydrate precursor ($VOHPO_4 \cdot 1/2H_2O$) from a pentavalent vanadium compound (e.g., $V_2O_5$), a pentavalent or trivalent phosphorus compound (e.g., ortho- and/or pyrophosphoric acid, phosphates or phosphorus acid), and a reductive alcohol (e.g., isobutanol), isolation of the precipitate and drying, with shaping (e.g., tableting) where appropriate; and (2) preactivation to give vanadyl pyrophosphate (($VO)_2 P_2O_7$) by calcination.

A variety of processes for preparing the VPO catalyst precursor are known. They differ primarily (i) in the nature of the reductive alcohol, (ii) in the presence or absence of additional components such as promoters, modifiers or pore formers, (iii) in the sequence and time of addition of the individual components in conjunction with the chosen temperatures, and (iv) in the isolation of the catalyst precursor formed.

EP-A 0 151 912 teaches the preparation of a VPO catalyst precursor for which vanadium pentoxide is reacted with phosphoric acid in the presence of isobutanol and a modifier selected from the group consisting of hydrogen iodide, sulfur dioxide, fuming sulfuric acid, and surfactants. The mixture is heated under reflux and the catalyst precursor is subsequently isolated by distillative removal of the solvent or by filtration.

EP-A 0 221 876, WO 94/04269, and U.S. Pat. No. 4,147,661 described the preparation of a VPO catalyst precursor for which phosphoric acid, isobutanol, vanadium pentoxide, and a promoter component are reacted in the presence of a hydrogen chloride gas infeed. The catalyst precursor is isolated by distillative removal of the solvent or by filtration.

The addition of the abovementioned modifiers has the critical disadvantage that hydrogen halides, sulfur dioxide, and fuming sulfuric acid are highly corrosive compounds, which necessitate a considerable complexity in terms of the required apparatus, and when surfactants are used there is a risk of foaming, with the attendant safety risks. Moreover, the addition of the modifiers may result in impurities in the precipitated catalyst precursor, these impurities possibly having an adverse effect on catalyst performance (activity, selectivity, space-time yield, lifetime).

Isolating the catalyst precursor by distillative removal of the solvent, moreover, has the disadvantage that all impurities which are not readily volatile, such as nonvolatile degradation products of the alcohol, for example, and impurities introduced with the reactant components, will remain in the precursor. In the course of subsequent calcination, there is then a risk, for example, of uncontrolled decomposition or oxidation of the thermally labile and oxidation-sensitive components and also of an uncontrolled reduction of the vanadium by these components. In all of the stated cases there is a risk of irreversible damage to the catalyst. In addition, because of the phosphorus excess normally employed, the catalyst precursor obtained by distillative removal of the solvent includes volatile phosphorus components, which during calcination or during start up of the oxidation reaction are liberated and may lead to unwanted deposits.

U.S. Pat. No. 5,274,996 teaches the preparation of a VPO catalyst precursor by combining isobutanol, oxalic acid, vanadium pentoxide, and phosphoric acid at room temperature, heating the mixture under reflux, distilling off some of the solvent, where appropriate, and isolating the catalyst precursor by decanting or filtering the cooled mixture.

U.S. Pat. No. 4,333,853 and EP-A 0 056 183 disclose the preparation of a VPO catalyst precursor by combining vanadium pentoxide, isobutanol, and orthophosphoric acid or, respectively, a mixture of orthophosphoric and pyrophosphoric acids, heating the mixture under reflux, cooling the resulting suspension, and isolating the precursor by filtration.

EP-A 0 031 696 teaches the preparation of a VPO catalyst precursor by reducing vanadium pentoxide with isobutanol under reflux, separating the undissolved vanadium components, adding phosphoric acid, heating the mixture under reflux, cooling the resultant suspension, and isolating the precursor by filtration.

U.S. Pat. No. 5,922,637 discloses the preparation of a Mo-promoted VPO catalyst precursor by reducing vanadium pentoxide in the presence of a molybdous promoter component with isobutanol/benzyl alcohol at 77° C., cooling the reaction mixture to 30° C., adding phosphoric acid, heating the mixture under reflux, cooling the resultant suspension, and isolating the precursor by filtration.

EP-A 0 804 963 and U.S. Pat. No. 4,668,652 disclose the preparation of a VPO catalyst precursor by heating a solution of isobutanol and phosphoric acid to boiling temperature under reflux, adding a suspension of vanadium pentoxide in isobutanol to the hot solution, continuing to heat the mixture under reflux, cooling the resultant suspension, and isolating the precursor by filtration.

EP-A 0 799 795, U.S. Pat. No. 4,064,070 and U.S. Pat. No. 4,132,670 describe the preparation of a VPO catalyst precursor for which a suspension of vanadium pentoxide and isobutanol or, respectively, isobutanol/benzyl alcohol is heated at boiling temperature under reflux for several hours and then phosphoric acid is supplied to the hot mixture. The mixture is heated further under reflux for several hours and then cooled, and the precursor is isolated.

WO 95/26817 teaches the preparation of a Fe- and Sb-promoted VPO catalyst precursor by combining vanadium pentoxide, isobutanol, benzyl alcohol, and a ferrous and antimonial promoter component, heating the mixture under reflux, adding phosphoric acid dropwise to the heated suspension, continuing to heat the suspension under reflux, and isolating the precursor by filtration.

Isolating the precursor by decanting has the disadvantage that only some of the liquid phase can be removed in this way and the remaining portion is stripped off in the course of subsequent drying by evaporation. This is attended by the disadvantages referred to above in the context of the distillative removal of the solvent.

In accordance with the invention it was recognized that during implementation of the processes described therein the precursor is isolated by filtration following precipitation, on the industrial scale, i.e., the 100 kg or metric ton scale, the grave disadvantage existed of very long filtration times, ranging from many days to a few weeks. As a result, the necessary apparatus is blocked for a long period of time and the production time for very large amounts of catalyst precursor is massively prolonged.

It is an object of the present invention to find a process for preparing a vanadium, phosphorus, and oxygen catalyst precursor for preparing maleic anhydride by heterogeneously catalyzed gas-phase oxidation of a hydrocarbon having at least four carbon atoms that does not possess the disadvantages described above, is easy to carry out industrially, and allows the catalyst precursor to be isolated rapidly and efficiently, even on the industrial scale, and, following a preactivation which is likewise easy to carry out industrially, leads to a catalyst of high activity and high selectivity.

We have found that this object is achieved by a process for preparing a vanadium, phosphorus, and oxygen catalyst precursor for preparing maleic anhydride by heterogeneously catalyzed gas-phase oxidation of a hydrocarbon having at least four carbon atoms, by reacting vanadium pentoxide (I) in the presence of a primary or secondary, noncyclic or cyclic, unbranched or branched, saturated alcohol having from 3 to 6 carbon atoms (II) with a pentavalent or trivalent phosphorus compound (III) in a temperature range from 80 to 160° C. with stirring and subsequently filtering the resultant suspension, which comprises using at least two of the following measures—

(a) (i) adding the phosphorus compound (III) to the vanadium pentoxide (I), suspended in the alcohol (II) and heated to 50 to 160° C., the time of contact between the vanadium pentoxide (I) and the alcohol (II) prior to commencement of the addition of the phosphorus compound (III) at a temperature $\geq 50°$ C. being $\leq 1$ hour; or
(ii) combining the vanadium pentoxide (I) with the phosphorus compound (III) in the presence of the alcohol (II) at a temperature of $\geq 0°$ C. and $<50°$ C. and then heating the combined compounds at a rate of $\geq 1.5°$ C./min to a temperature of 50 to 160° C.;
(b) during the reaction of the vanadium pentoxide (I) in the presence of the alcohol (II) with the phosphorus compound (III), exposing the reaction mixture to a stirring power of from 0.01 to 0.6 W/kg suspension, the calculation of the stirring power being based on the physicochemical properties of the mixed reactants prior to reaction and at 20° C.; and
(c) filtering at a temperature of from 65° C. to 160° C.—to set a filtration resistance of $\leq 50 \cdot 10^{13}$ mPa·s/m².

At the heart of the invention is the setting of a filtration resistance $\alpha_H \cdot \eta$ of $\leq 50 \cdot 10^{13}$ mPa·s/m² during the filtration of the suspension obtained by reacting vanadium pentoxide (I) in the presence of the alcohol (II) with the phosphorus compound (III), said resistance being set by at least two measures from the series (a), (b) and (c).

The filtration resistance $\alpha_H \cdot \eta$ is a parameter which is general knowledge in relation to the filterability of suspensions at a given temperature and is described, for example, in VDI [German Engineers Association] Guideline 2762 "Filterability of suspensions/determination of filtercake resistance" by the Verein Deutscher Ingenieure [VDI], February 1997. It is composed of the product of the specific filter resistance based on the filtercake height, $\alpha_H$, and the dynamic viscosity, $\eta$. The smaller the filtration resistance $\alpha_H \cdot \eta$, the better, generally, the filterability of the suspension.

The filtration resistance $\alpha_H \cdot \eta$ is determined in accordance with the abovementioned VDI Guideline 2762. A representative sample of the suspension is placed in a pressure filter with a filter area of at least 20 cm² and a capacity of at least 300 mL and is filtered by provision of a constant differential pressure at the desired filtration temperature. The end of the filtration is evident by an evening-out of the differential pressure owing to the formation of cracks in the filtercake. The relationship governing the evaluation is given by the formula (IV)

$$t = \frac{A \cdot H_{end} \cdot \alpha_H \cdot \eta}{2 \cdot V_{end} \cdot A^2 \cdot \Delta p} \cdot V^2(t) + \frac{R_T \cdot \eta}{A \cdot \Delta p} \cdot V(t) \qquad (IV)$$

in which the constants and variables are defined as follows:
t time from start of filtration
A filter area
$H_{end}$ height of filtercake at end of filtration
$\alpha_H \cdot \eta$ filtration resistance
$V_{end}$ total filtrate volume
$\Delta p$ pressure difference
V(t) filtrate volume at time t
$R_T$ filter resistance
$\eta$ dynamic viscosity.

In the process of the invention it is preferred to set a filtration resistance $\alpha_H \cdot \eta$ of $\leq 25 \cdot 10^{13}$ mPa·s/m², with particular preference $\leq 20 \cdot 10^{13}$ mPa·s/m², and with very particular preference $\leq 10 \cdot 10^{13}$ mPa·s/m².

Measure (a)

One of the inventive measures for setting a filtration resistance $\alpha_H \cdot \eta$ of $\leq 50 \cdot 10^{13}$ mPa·s/m² relates to the way in which the vanadium pentoxide (I) component and the phosphorus compound (III) component are combined. Surprisingly, the following two alternative measures have been found:

Measure (a)(i)

With measure (a)(i), the phosphorus compound (III) is added to the vanadium pentoxide (I) which has been suspended in the alcohol (II) and heated to 50 to 160° C., preferably 60 to 160° C., and with particular preference to 80 to 160° C., the time of contact between the vanadium pentoxide (I) and the alcohol (II) prior to commencement of the addition of the phosphorus compound (III) at, a temperature $\geq 50°$ C. being $\leq 1$ hour. The addition is generally made with mixing, preferably with stirring.

The time of contact between the vanadium pentoxide (I) and the alcohol (II) prior to commencement of the addition of the phosphorus compound (III) at a temperature $\geq 50°$ C. is preferably $\leq 45$ minutes and with particular preference $\leq 30$ minutes. In one particularly preferred variant, the vanadium pentoxide (I) heated to $\geq 50°$ C. is prepared by combining vanadium pentoxide (I) conditioned at $\geq 0°$ C. and $<50°$ C. with the alcohol (II) conditioned at from 50 to $160°$ C.

The combining is generally conducted in the reaction apparatus suitable for the subsequent reaction, such as a stirred tank, with mixing.

The phosphorus compound (III) can be added in neat or diluted form. Where the phosphorus compound (III) is added in diluted form, a mixture with the alcohol (II) is preferred. In order to lower the viscosity it may be advantageous to condition the phosphorus compound (III) to be added to a temperature in the range from 40 to $100°$ C., preferably from 40 to $60°$ C.

In one possible variation, a suspension of vanadium pentoxide (I) in alcohol (II) is charged to the reaction apparatus and is then brought to a temperature of 50 to $160°$ C. The phosphorus compound (III), diluted where appropriate with the alcohol (II), is subsequently supplied to this suspension with stirring. In order to lower the viscosity of the phosphorus compound (III) to be supplied it may be advantageous to condition it to a temperature in the range from 40 to $100°$ C.

In another possible variation, the alcohol (II) is introduced initially and then brought preferably to a temperature of 50 to $160°$ C. Thereafter, vanadium pentoxide is supplied with stirring, in the form of a solid or, where appropriate, in the form of a suspension in alcohol (II) and the phosphorus compound (III) as well, which may where appropriate have been diluted with the alcohol (II), is supplied with stirring.

Where appropriate, the vanadium pentoxide or its suspension may likewise have been conditioned to an elevated temperature, from 50 to $160°$ C. for example. In order to lower the viscosity of the phosphorus compound (III) to be supplied it may be advantageous to condition it to a temperature in the range from 40 to $100°$ C. Commencement of the addition of the phosphorus compound (III) may accompany the supplying of the vanadium pentoxide (I). Preferably, the addition of the phosphorus compound (III) is commenced after from about 10 to 100% and with particular preference from about 50 to 100% of the total amount of vanadium pentoxide (I) has been added.

Measure (a)(ii)

With measure (a)(ii), the vanadium pentoxide (I) is combined with the phosphorus compound (III) in the presence of the alcohol (II) at a temperature of $\geq 0°$ C. and $<50°$ C. and the mixture is subsequently heated to a temperature of 50 to $160°$ C. at a rate of $\geq 1.5°$ C./min. The combining and the subsequent heating take place in general with mixing, preferably with stirring.

The temperature range specified with the combining of the vanadium pentoxide (I) with the phosphorus compound (III) in the presence of the alcohol (II) refers to the mixing temperature which is attained in each case. The individual components may be at different temperatures. Combining takes place preferably at a temperature of from 10 to $45°$ C. and with particular preference at a temperature from 20 to $40°$ C.

The components are generally combined in the reaction apparatus suitable for the subsequent reaction, a stirred tank, for example, with mixing.

The sequence of the addition of the individual components is generally unimportant. For example, it is possible to introduce the alcohol (II) initially and to feed in the vanadium pentoxide (I) and the phosphorus compound (III) in parallel or successively. Furthermore, it is also possible to introduce the phosphorus compound (III), where appropriate as a mixture with the alcohol (II), initially and to feed in the vanadium pentoxide (I) and any further alcohol (II) together or successively. Moreover, it is also possible to introduce the vanadium pentoxide (I) as a suspension in alcohol (II) and to feed in the phosphorus compound (III). Combining and subsequently heating generally take place with mixing, preferably with stirring.

The phosphorus compound (III) may be added in neat or diluted form. Where the phosphorus compound (III) is added in diluted form, a mixture with the alcohol (II) is preferred. In order to lower the viscosity it may be advantageous to condition the phosphorus compound (III) to be added to a temperature in the range from 40 to $100°$ C., preferably from 40 to $60°$ C.

The resultant mixture is subsequently heated to a temperature of 50 to $160°$ C., preferably from 60 to $160°$ C., and with particular preference from 80 to $160°$ C. at a rate of $\geq 1.5°$ C./min and preferably $\geq 2°$ C./min.

It should be pointed out that within the context of the present invention, measure (a) is optional subject to the proviso that measures (b) and (c) are performed. In the text below, therefore, a number of further possible variations of the combining are described which do not come under the inventive measure (a) but which may nevertheless be carried out subject to the above proviso.

In one of the variations of the combining which does not come under the inventive measure (a), the vanadium pentoxide (I) is combined with the phosphorus compound (III) in the presence of the alcohol (II) at a temperature of $\geq 0°$ C. and $<50°$ C. and the mixture is subsequently heated to a temperature of 50 to $160°$ C. at a rate of $<1.5°$ C./min. The combining and the subsequent heating take place generally with mixing, preferably with stirring.

In a further variation of the combining which does not come under the inventive measure (a), the phosphorus compound (III), which may where appropriate have been diluted with the alcohol (II), is introduced initially and is then brought preferably to a temperature of 50 to $160°$ C. Thereafter, vanadium pentoxide (I) is fed in, as a solid or, where appropriate, in the form of a suspension in the alcohol (II). The vanadium pentoxide (I) or its suspension may where appropriate have been conditioned likewise to an elevated temperature, from 50 to $160°$ C. for example. The combining takes place generally with mixing, preferably with stirring.

During the preparation of the catalyst precursor it is also possible to add what are known as promoter components. Suitable promoters are the elements from groups 1 to 15 of the periodic system, and also compounds thereof. Suitable promoters are described, for example, in WO 97/12674 and WO 95/26817 and also in U.S. Pat. No. 5,137,860, U.S. Pat. No. 5,296,436, U.S. Pat. No. 5,158,923, and U.S. Pat. No. 4,795,818. Preferred promoters are compounds of the elements cobalt, molybdenum, iron, zinc, hafnium, zirconium, lithium, titanium, chromium, manganese, nickel, copper, boron, silicon, antimony, tin, niobium, and bismuth, with particular preference molybdenum, iron, zinc, antimony, bismuth, and lithium. The promoted catalysts may comprise one or more promoters. Generally speaking, the promoter components are added before, during or after the reaction of the vanadium pentoxide (I) in the presence of the alcohol (II) with the phosphorus compound (III). The total promoter content of the finished catalyst is generally not more than about 5% by weight, calculated in each case as the oxide.

Examples of suitable promoter components are the acetates, acetylacetonates, oxalates, oxides or alkoxides of the aforementioned promoter metals, such as cobalt(II) acetate, cobalt(II) acetylacetonate, cobalt(II) chloride, molybdenum(VI) oxide, molybdenum(III) chloride, iron (III) acetylacetonate, iron(III) chloride, zinc(II) oxide, zinc (II) acetylacetonate, lithium chloride, lithium oxide, bismuth (III) chloride, bismuth(III) ethylhexanoate, nickel(II) ethylhexanoate, nickel(II) oxalate, zirconyl chloride, zirconium(IV) butoxide, silicon(IV) ethoxide, niobium(V) chloride, and niobium(V) oxide. For further details refer to the aforementioned WO OPI documents and U.S. patents.

The relative molar ratio of the phosphorus compound (III) to the vanadium pentoxide (I) is generally set in accordance with the ratio desired in the catalyst precursor. The molar phosphorus/vanadium ratio in the reaction mixture for preparing the catalyst precursor is preferably from 1.0 to 1.5 and with particular preference from 1.1 to 1.3.

The amount of the alcohol (II) should advantageously lie beyond the amount required stoichiometrically for reducing the vanadium from oxidation state +5 to an oxidation state in the range from +3.5 to +4.5. The amount should further be such that with the vanadium pentoxide (I) it is possible to form a suspension which allows intensive mixing with the phosphorus compound (III). The molar ratio of the alcohol (II) to the vanadium pentoxide (I) is generally from 10 to 25 and preferably from 12 to 20.

When the vanadium pentoxide (I), alcohol (II), and phosphorus compound (III) components have been combined, the mixture is heated at a temperature from 80 to 160° C. for a period of usually several hours under mixing, preferably with stirring, in order for said compounds to react. The temperature range to be chosen is dependent on a variety of factors, one example being the boiling point of the added alcohol (II), and can be optimized by means of simple experiments. The volatile compounds, such as water, the alcohol (II) and its degradation products, such as aldehyde or carboxylic acid, for example, evaporate from the reaction mixture and can either be taken off or else fully or partially condensed and recycled. Preference is given to full or partial recycling by heating under reflux. Full recycling is particularly preferred. The reaction at elevated temperature generally takes several hours and is dependent on a variety of factors, such as the nature of the added components or the temperature, for example. Moreover, the temperature and the chosen period of heating within a certain range may also be used to set and influence the properties of the catalyst precursor. The parameters of temperature and time can easily be optimized for an existing system by means of a few experiments. The time normally required for said reaction is from 1 to 25 hours.

Measure (b)

Another of the inventive measures for setting a filtration resistance $\alpha_H \eta$ of $\leq 50 \cdot 10^{13}$ mPa·s/m$^2$ is the exposing of the reaction mixture in the reaction of the vanadium pentoxide (I) in the presence of the alcohol (II) with phosphorus compound (III) to a stirring power of from 0.01 to 0.6 W/kg suspension, the calculation of the stirring power being based on the physicochemical properties of the mixed reactants prior to the reaction and at 20° C.

The stirring power is the power per unit mass of suspension which acts on the suspension as a result of stirring. The stirring power is a parameter for the stirring of solutions and suspensions that is well known from the field of stirring technology. It is described, for example, in Werner Hemming, "Verfahrenstechnik" from the "Kamprath-Reihe Technik, kurz und bündig", Vogel-Verlag, Würzburg, 1975, ISBN 3-8023-0084-X, Section 6.1.1 and also in Marko Zlokarnik, "Rührtechnik—Theorie und Praxis", Springer-Verlag Berlin 1999, Section 2.1, pages 73 to 79.

Where the dimensionless performance coefficient $N_e$ is known, the stirring power P can be calculated by formula (V)

$$P = N_e \cdot \rho \cdot d^5 \cdot n^3 \qquad (V),$$

where ρ stands for the average density of the suspension, d for the diameter of the stirrer, and n for the rotary speed of the stirrer. The dimensionless performance coefficient $N_e$ is system-dependent and can be determined, where the stirrer form and the modified dimensionless Reynolds number $Re_M$ $$Re_M = \frac{n \cdot d^2}{\nu} \qquad (VI)$$

are known, where ν stands for the kinematic viscosity and n and d are as defined above, from the diagram for determining the performance characteristics. Such a diagram is contained, for example, in Marko Zlokarnik, "Rührtechnik—Theorie und Praxis", Springer-Verlag Berlin 1999, page 77, FIG. 2.2.

When calculating the stirring power, the physicochemical properties of the mixed reactants that are used, namely the kinematic viscosity ν and the density ρ, are those prior to the reaction and at 20° C.

In the context of measure (b) in the process of the invention it is preferred to employ a stirring power of from 0.01 to 0.5 W/kg suspension, with particular preference from 0.02 to 0.5 W/kg suspension, and with very particular preference from 0.05 to 0.4 W/kg suspension.

The process of the invention can in principle be carried out using different stirrer geometries. In accordance with the viscosity range of the suspension to be stirred, however, preference is given to disc stirrers, impeller stirrers, pitched-blade stirrers, propeller stirrers, and modifications thereof. Depending on the batch size and on the volume and geometry of the stirring vessel, it may be advantageous to use a stirrer having two or more—two or three, for example—stirring elements attached to the stirring shaft. In this case, the stirrer is referred to as a multistage stirrer. Stirring generally takes place in the presence of one or more flow disrupters.

It should be pointed out that in the context of the present invention, measure (b) is optional subject to the proviso that measures (a) and (c) are performed. In this case it is also possible, for example, to employ a much higher stirring power when reacting the vanadium pentoxide (I) in the presence of the alcohol (II) with phosphorus compound (III).

After the end of the reaction of the vanadium pentoxide (I) in the presence of the alcohol (II) with the phosphorus compound (III), the precipitate formed is filtered off, filtration possibly being preceded where appropriate by a cooling phase and also a storage phase or aging phase of the cooled reaction mixture.

Measure (c)

The third of the inventive measures for setting a filtration resistance $\alpha_H \cdot \eta$ of $\leq 50 \cdot 10^{13}$ mPa·s/m² is the filtration of the resulting precipitate at a temperature of from 65° C. to 160° C. The filtration takes place preferably at a temperature of from 70 to 160° C. and with particular preference at a temperature of from 80 to 160° C.

In the process of the invention, the filtration may in principle be carried out in the known apparatus suitable for filtration. examples that may be mentioned of suitable apparatus include suction filters, plate filters, and centrifuges (e.g., bag filter centrifuges). It is preferred to use a suction filter. Suitable filter media that may be mentioned include filter papers, porous filter films, close-knit meshes, and woven fabrics, with close-knit meshes and woven fabrics generally being preferred. Preference is given to implementing a pressure filtration.

Particular preference is given to the use for suitable pressure suction filter, which in one especially preferred embodiment is equipped with a heatable stirrer. The heatable stirrer here may serve to swirl up the suspension, to spread the filtercake smoothly, to introduce heat during the subsequent drying operation, and for loosening during product discharge.

The isolated precipitate can be processed further with or without washing. Washing of the isolated precipitate has the advantage that adhering residues of the alcohol (II) and also its degradation products can be reduced further. examples that may be mentioned of suitable solvents for the washing operation include alcohols, aliphatic and/or aromatic hydrocarbons (e.g., pentane, hexane, petroleum spirits, benzene, toluene, xylenes), ketones (e.g., 2-propanone (acetone), 2-butanone, 3-pentanone), ethers (e.g., 1,2-dimethoxyethane, tetrahydrofuran, 1,4-dioxane) or mixture thereof. If the isolated precipitate is washed, then it is preferred to use the alcohol (II) selected for the reaction beforehand.

It should be pointed out that in the context of the present invention measure (c) is optional subject to the proviso that measures (a) and (b) are performed. In this case it is also possible, for example, to conduct the filtration of the resulting precipitate at a much lower temperature.

The filtration resistance $\alpha_H \cdot \eta$ is dependent inter alia on the temperature at which filtration is conducted and on the particle size distribution of the particles formed in the reaction of the vanadium pentoxide (I) in the presence of alcohol (II) with the phosphorus compound (III). This distribution is significantly influenced, in the context of the measures according to the invention, by the implementation of measure (a), measure (b), or both measures (a) and (b). The suspension obtainable when carrying out the process of the invention preferably has a volume fraction of particles $\leq 10$ μm of $\leq 30\%$, with particular preference $\leq 20\%$, and very particular preference $\leq 10\%$. This particle size distribution is normally determined by laser diffraction spectrometry.

The isolated precipitate can be processed further in a variety of ways. For example, the isolated precipitate can be processed further wet, dried, or having been conditioned beforehand, there generally being a fluid transition between drying and prior conditioning.

Drying is generally regarded as comprising a temperature treatment in the range from 30 to 250° C., carried out in general at a pressure from 0.0 ("vacuum") to 0.1 MPa abs ("atmospheric pressure"). With vacuum drying it is generally possible to employ a lower temperature than when drying under atmospheric pressure. The gas atmosphere above the product during drying may comprise oxygen, steam and/or inert gases, such as nitrogen, carbon dioxide or noble gases. Drying is preferably conducted under a pressure of from 1 to 30 kPa abs at a temperature from 50 to 200° C. under an oxygenous or oxygen-free residual gas atmosphere, such as air or nitrogen, for example. Drying may be conducted, for example, in the apparatus used for the filtration or in a separate apparatus, a drying oven or a continuously operating belt drier, for example. Drying is preferably carried out in the apparatus used for the filtration.

Prior conditioning is generally considered to refer to a temperature treatment in the range from 200 to 350° C., preferably from 250 to 350° C. Conditioning may in principle be carried out within a wide range of pressures, the application with low pressures generally promoting the removal of organic components.

The conditioning is generally conducted at a pressure from 0.0 ("vacuum") to 0.15 MPa abs, preferably at approximately 0.1 MPa abs ("atmospheric pressure"). Conditioning generally takes from several minutes to several hours and is dependent on a number of factors, such as the concentration of the phosphorus compound (III) used, the nature of the alcohol (II) used, the further treatment of the deposited precipitate (e.g., aging of the precipitate), and the conditioning temperature selected. For example, it is possible for long conditioning at a low temperature to give a similar result to shorter conditioning at a moderate or higher temperature. For a given system, the parameters of temperature and time can be optimized easily by means of a few experiments. Generally speaking, the conditioning time required is from 0.5 to 10 hours. The gas atmosphere present during conditioning may comprise oxygen, steam and/or inert gases, such as nitrogen, carbon dioxide or noble gases. Conditioning is preferably carried out under air.

Conditioning can be conducted batchwise or continuously, for example. Suitable apparatus that may be mentioned includes drying ovens, muffle furnaces, belt calcining means, fluid-bed dryers or rotary tubes. In order to obtain a uniformly conditioned product, it is in general advantageous to employ a continuously operating conditioning process with mixing of the powder to be conditioned. Particular preference is therefore given to conditioning in a continuously operated rotary tube.

In the process of the invention, the isolated precipitate is preferably dried and then conditioned in an air atmosphere in a temperature range from 250 to 350° C.

The product prepared by the process described above is generally shaped into particles having an averaged diameter of at least 2 mm and preferably at least 3 mm. The averaged diameter of a particle is the average of the smallest and the largest dimensions between two plane-parallel plates.

By particles are meant both irregularly shaped particles and also geometrically shaped particles, referred to as moldings. The conditioned product obtained from step (c) is preferably shaped into moldings. examples of suitable moldings that may be mentioned include tablets, cylinders, hollow cylinders, beads, strands, wagon wheels, and extrudates. Special shapes, such as trilobes and tristars (see WO 93/01155) or moldings with at least one notch on the outside (see U.S. Pat. No. 5,168,090), for example, are likewise possible.

Shaping takes place preferably by tableting, normally using the dried and preferably preconditioned catalyst precursor powder. Moldings for preferred production that may be mentioned include tablets, cylinders and hollow cylinders. For tableting, a tableting aid is generally added to the powder and the components are intimately mixed. Tableting aids are generally inert catalytically and enhance the tableting properties of the powder, by raising the sliding properties and free-flow properties, for example. One suitable, preferred tableting aid that may be mentioned is graphite. The added tableting aids generally remain in the activated catalyst. The amount of tableting aid in the finished catalyst is typically from about 2 to 6% by weight.

With particular preference, the moldings shaped have a substantially hollow cylindrical structure. A substantially hollow cylindrical structure is a structure which substantially comprises a cylinder having an aperture which is continuous between the two end faces. The cylinder is characterized by two substantially parallel end faces and one lateral surface, with the cross section of the cylinder, i.e., parallel to the end faces, being substantially of circular structure. The cross section of the continuous aperture, i.e., parallel to the end faces of the cylinder, is likewise substantially of circular structure. The continuous aperture is preferably central with respect to the end faces, although this does not exclude other spatial arrangements.

The term "substantially" indicates that deviations from the ideal geometry, such as slightly deformations in the circular structure, end faces which are not in plane-parallel alignment, flaked-off angles and edges, surface roughness or notches in the lateral surface, in the end faces, or in the inner surface of the continuous hole, are embraced in the catalyst of the invention. Within the bounds of the accuracy of the tableting art, circular end faces, a circular cross section of the continuous hole, end faces in parallel alignment, and macroscopically smooth surfaces are preferred.

The substantially hollow cylindrical structure can be described by an external di0ameter $d_1$, a height h of the distance between the two end faces, and an internal-hole (continuous-aperture) diameter $d_2$. The external diameter $d_1$ is preferably from 3 to 10 mm, with particular preference from 4 to 8 mm, with very particular preference from 4.5 to 6 mm. The height h is preferably from 1 to 10 mm, with particular preference from 2 to 6 mm, with very particular preference from 2 to 3.5 mm. The continuous-aperture diameter $d_2$ is preferably from 1 to 8 mm, with particular preference from 2 to 6 mm, with very particular preference from 2 to 3 mm. Particular preference is given to a hollow cylindrical structure which has (a) a ratio of the height h to the continuous-aperture diameter $d_2$ of not more than 1.5 and (b) a ratio of the geometric surface area $A_{geo}$ to the geometric volume $V_{geo}$ of at least 2 $mm^{-1}$, as described for instance in WO 01/68245.

In the process of the invention, a filtration resistance $\alpha_H \cdot \eta$ of $\leq 50 \cdot 10^{13}$ mPa·s/m$^2$ is set by implementing at least two of the inventive measures from the series (a), (b), and (c). For the purposes of the invention it is unimportant which two of the inventive measures are implemented. At this point it may be pointed out once again that for measure (a) there are two alternative, inventive possibilities for combining the vanadium pentoxide (I), alcohol (II), and phosphorus compound (III) reactants, namely variant (i), referred to below for short as (a-i), and variant (ii), referred to below for short as (a-ii).

Possible combinations of the inventive measures that may be mentioned explicitly are: (a-i) and (b), (a-i) and (c), (b) and (c), (a-i) and (b) and (c), (a-ii) and (b), (a-ii) and (c), and also (a-ii) and (b) and (c).

Of the abovementioned seven combinations, those combinations which include the variant (a-i) or (a-ii) are preferred. These preferred combinations are: (a-i) and (b), (a-i) and (c), (a-i) and (b) and (c), (a-ii) and (b), (a-ii) and (c), and also (a-ii) and (b) and (c).

Particular preference is given to the combinations which include variant (a-i) and also to the combinations which include all three inventive measures (a), (b), and (c). These preferred combinations are: (a-i) and (b), (a-i) and (c), (a-i).and (b) and (c), and also (a-ii) and (b) and (c).

Very particular preference is given to the combinations which include all three inventive measures (a), (b), and (c). These very particularly preferred combinations are: (a-i) and (b) and (c), and also (a-ii) and (b) and (c), especially (a-i) and (b) and (c).

The vanadium pentoxide (I) is used preferably in the form of a powder, with particular preference in a particle range from 50 to 500 μm. Where much larger particles are present, the solid is comminuted before being used, and is sieved where appropriate. examples of suitable apparatus include ball mills and planetary mills.

The primary or secondary, noncyclic or cyclic, unbranched or branched, saturated alcohol (II) having from 3 to 6 carbon atoms that is used in the process of the invention is generally a primary or secondary, unbranched or branched $C_3$ to $C_6$ alkanol, cyclopentanol, cyclohexanol or a mixture thereof. Suitable alcohols include n-propanol (1-propanol), isopropanol (2-propanol), n-butanol (1-butanol), sec-butanol (2-butanol), isobutanol (2-methyl-1-propanol), 1-pentanol, 2-pentanol, 3-pentanol, 2-methyl-1-butanol, 3-methyl-1-butanol, 3-methyl-2-butanol, 2,2-dimethyl-1-propanol, 1-hexanol, 2-hexanol, 3-hexanol, 2-methyl-1-hexanol, 3-methyl-1-pentanol, 4-methyl-1-pentanol, 3-methyl-2-pentanol, 4-methyl-2-pentanol, 2,2-dimethyl-1-butanol, 2,3-dimethyl-1-butanol, 3,3-dimethyl-1-butanol, 3,3-dimethyl-2-butanol, cyclopentanol, cyclohexanol, and mixtures thereof. Particular preference is given to using primary, unbranched or branched $C_3$ to $C_5$ alkanols and also cyclohexanol. Very particular preference is given to n-propanol (1-propanol), n-butanol (1-butanol), isobutanol (2-methyl-1-propanol), 1-pentanol, 2-methyl-1-butanol, 3-methyl-1-butanol, and cyclohexanol, especially isobutanol.

Examples of suitable pentavalent or trivalent phosphorus compounds (III) include ortho-, pyro-, and polyphosphoric acid, phosphates, and phosphorus acid. It is preferred to use a pentavalent phosphorus compound, with particular preference orthophosphoric acid ($H_3PO_4$), pyrophosphoric acid ($H_4P_2O_7$), polyphosphoric acid ($H_{n+2}P_nO_{3n+1}$ with $n \geq 3$) or a mixture thereof.

In one very particularly preferred embodiment, a mixture of ortho-, pyro-, and polyphosphoric acid having an arithmetic $H_3PO_4$ content of from 102 to 110% by weight, in particular from 104 to 106% by weight, is employed. The phosphoric acid to be employed is generally prepared by introducing phosphorus pentoxide into water or aqueous phosphoric acid with a strength, for example, of from 85 to 100%.

In one particularly preferred embodiment for the preparation of the catalyst precursor, a suspension of vanadium pentoxide in isobutanol is charged to a suitable stirred apparatus at a temperature of $\geq 0°$ C. and $<50°$ C. and from 102 to 110% strength phosphoric acid is fed in with stirring. Subsequently, with continuing stirring with a stirring power of from 0.01 to 0.6 W/kg suspension, the mixture is heated to a temperature from 80 to 120° C. at a rate of $\geq 1.5°$ C./min and is left under reflux conditions for several hours with continued stirring at the abovementioned stirring power. Subsequent to this the hot suspension is filtered, preferably in the stated temperature range from 80 to 120° C., and the solid product is washed with a little isobutanol and dried under reduced pressure at a temperature in the range from 100 to 200° C. The isolated and dried precipitate is then conditioned continuously, preferably in a rotary tube, in air at approximately atmospheric pressure in a temperature range from 250 to 350° C. with an average residence time in the region of 0.5 to 5 hours, preferably from 1 to 3 hours. The conditioned product obtained is then intimately mixed with from 2 to 6% by weight of graphite and is tabletted to give moldings in the form of tablets or hollow cylinders. The catalyst precursor is preferably tabletted to hollow cylinders having an external diameter $d_1$ of from 5 to 6 mm, a height h of from 3 to 4 mm, and a continuous-aperture diameter $d_2$ of from 2 to 3 mm.

In one very particularly preferred embodiment for the preparation of the catalyst precursor, a suspension of vanadium pentoxide in isobutanol, heated at from 50 to 120° C., is prepared in a suitable stirred apparatus. This suspension may be prepared in a variety of ways: for example, by combining vanadium pentoxide and isobutanol and then heating the mixture to the desired temperature or by introducing vanadium pentoxide into preheated isobutanol. Then, with stirring with a stirring power of from 0.01 to 0.6 W/kg suspension, from 102 to 110% strength phosphoric acid is fed into the suspension of vanadium pentoxide in isobutanol, heated at from 50 to 120° C. The mixture is subsequently left under reflux conditions for several hours, with stirring at the abovementioned stirring power and at a temperature of from 80 to 120° C., possibly preceded by heating in order to reach the temperature of from 80 to 120° C. Thereafter, the hot suspension is filtered, preferably in the stated temperature range from 80 to 120° C., and the solid product is washed with a little isobutanol and dried under reduced pressure at a temperature in the range from 100 to 200° C. The isolated and dried precipitate is then conditioned continuously, preferably in a rotary tube, in air at approximately atmospheric pressure and in a temperature range from 250 to 350° C. with an average residence time in the range from 0.5 to 5 hours, preferably from 1 to 3 hours. The conditioned product obtained is then intimately mixture with from 2 to 6% by weight of graphite and is tabletted to give moldings in the form of tablets or hollow cylinders. The catalyst precursor is preferably tabletted to hollow cylinders having an external diameter $d_1$ of from 5 to 6 mm, a height h of from 3 to 4 mm, and a continuous-aperture diameter $d_2$ of from 2 to 3 mm.

The invention further provides a catalyst precursor for preparing maleic anhydride by heterogeneously catalyzed gas-phase oxidation of a hydrocarbon having at least four carbon atoms, said precursor being obtainable by the process of the invention described above.

The process of the invention makes it possible to prepare a vanadium, phosphorus, and oxygen catalyst precursor for preparing maleic anhydride by heterogeneously catalyzed gas-phase oxidation of a hydrocarbon having at least four carbon atoms, the preparation of the catalyst precursor being easy to carry out industrially, the catalyst precursor being able to be isolated efficiently and rapidly in particular even on the industrial scale, and the precursor, as a selectivity-determining and activity-determining precursor, permitting the preparation of a catalyst having high activity and high selectivity. The rapid and efficient filtration makes a substantial contribution to a rapid and efficient production process of the overall catalyst precursor. For a given filtration capacity it is possible to achieve a much higher throughput.

The invention further provides a process for preparing a vanadium-phosphorus-oxygen catalyst for preparing maleic anhydride by heterogeneously catalyzed gas-phase oxidation of a hydrocarbon having at least four carbon atoms, by treating a vanadium, phosphorus, and oxygen catalyst precursor in at least one atmosphere comprising oxygen ($O_2$), hydrogen oxide ($H_2O$) and/or inert gas in a temperature range from 250 to 600° C., which comprises using as catalyst precursor a catalyst precursor of the invention as described above.

Examples that may be mentioned of suitable inert gases include nitrogen, carbon dioxide, and noble gases.

Calcination may be conducted batchwise, in a shaft furnace, tray furnace, muffle furnace or oven, for example, or continuously, in a rotary tube, belt kiln or rotary sphere furnace, for example. It may comprise successive, different sections in terms of temperature such as heating, temperature hold or cooling, and successive different sections in respect of the atmospheres, such as oxygenous, steam-containing or oxygen-free gas atmospheres. Suitable preactivation processes are described, for example, in U.S. Pat. No. 5,137,860 and U.S. Pat. No. 4,933,312 and in the OPI document WO 95/29006, which are hereby expressly incorporated by reference but without implying any limitation. Particular preference is given to continuous calcination in a belt kiln comprising at least two—for example, from two to ten—calcining zones which where appropriate have different gas atmospheres and different temperatures. By means of a suitable combination of temperatures, treatment times, and gas atmospheres, adapted to the respective catalyst system, it is possible to influence and therefore tailor the mechanical and catalytical quality of the catalyst.

In the context of the present invention, preference is given to a calcination wherein the catalyst precursor (i) is heated to a temperature from 200 to 350° C. in at least one calcining zone in an oxidizing atmosphere having an oxygen content of from 2 to 21% by volume and is left under these conditions until the vanadium has the desired average oxidation state; and (ii) is heated to a temperature from 300 to 500° C. in at least one further calcining zone in a nonoxidizing atmosphere having an oxygen content of $\leq 0.5\%$ by volume and a hydrogen oxide content of from 20 to 75% by volume and is left under these conditions for $\geq 0.5$ hour.

In step (i), the catalyst precursor is left at a temperature from 200 to 350° C. and preferably from 250 to 350° C. in an oxidizing atmosphere having a molecular oxygen content of generally from 2 to 21% by volume and preferably from 5 to 21% by volume for a period which is effective to set the desired average oxidation state of the vanadium. Generally in step (i) mixtures of oxygen, inert gases (e.g., nitrogen or argon), hydrogen oxide (steam) and/or air, and also air itself, are employed. From the standpoint of the catalyst precursor passed through the calcining zone or zones, the temperature during the calcining step (i) can be kept constant or may on average rise or fall. Since step (i) is generally preceded by a heating phase, the temperature will generally first rise before then leveling off at the desired end value. In general, therefore, the calcining zone of step (i) is preceded by at least one further calcining zone for the purpose of heating the catalyst precursor.

In the process of the invention, the time for which the conditioning in step (i) is maintained is preferably selected such that an average vanadium oxidation state is set at a level of from +3.9 to +4.4, preferably from +4.0 to +4.3.

Since it is extremely difficult, for reasons associated with the apparatus and time, to determine the average oxidation state of the vanadium during the calcining operation, the period of time necessary is advantageously determined experimentally in preliminary experiments. For this purpose a series of measurements is generally used in which conditioning is carried out under defined conditions, the samples being removed from the system after different times, cooled, and analyzed for the average oxidation state of the vanadium.

The period of time required in the case of step (i) is generally dependent on the nature of the catalyst precursor, on the set temperature, and on the chosen gas atmosphere, particularly on the oxygen content. In general, the time for step (i) extends to a duration of more than 0.5 hour and preferably more than 1 hour. Generally speaking, a period of up to 4 hours, preferably of up to 2 hours, is sufficient to set the desired average oxidation state. Under appropriately set conditions (e.g., lower range of the temperature span and/or low molecular oxygen content), however, it is possible for a period of more than 6 hours to be necessary.

In step (ii), the resultant catalyst intermediate is left at a temperature from 300 to 500° C. and preferably from 350 to 450° C. in a nonoxidizing atmosphere having a molecular oxygen content of $\leq 0.5\%$ by volume and a hydrogen oxide (steam) content of from 20 to 75% by volume, preferably from 30 to 60% by volume, for a period of $\geq 0.5$ hour, preferably from 2 to 10 hours, and with particular preference from 2 to 4 hours. In addition to the hydrogen oxide mentioned, the nonoxidizing atmosphere generally comprises predominantly nitrogen and/or noble gases, such as argon, for example, although this is not intended to denote any restriction. Gases such as carbon dioxide, for example, are also suitable in principle. The nonoxidizing atmosphere preferably contains $\geq 40\%$ by volume nitrogen. From the standpoint of the catalyst precursor passed through the calcining zone or zones, the temperature during the calcining step (ii) can be kept constant or may on average rise or fall. Where step (ii) is conducted at a higher or lower temperature than step (i), there is generally a heating or cooling phase between steps (i) and (ii), said phase being implemented where appropriate in a further calcining zone. In order to permit improved separation from the oxygenous atmosphere of step (i), this further calcining zone between (i) and (ii) may be flushed with inert gas, such as nitrogen, for example. Step (ii) is preferably conducted at a temperature higher by from 50 to 150° C. than step (i).

The calcination generally comprises a further step (iii), to be carried out later than step (ii), in which the calcined catalyst precursor is cooled in an inert gas atmosphere to a temperature of $\leq 300°$ C., preferably less than $\leq 200°$ C., and with particular preference $\leq 150°$ C.

Further steps are possible before, between and/or after steps (i) and (ii), or (i), (ii), and (iii), in the context of calcination in accordance with the process of the invention. Without limitation, further steps that may be mentioned include, for example, changes in temperature (heating, cooling), changes in the gas atmosphere (changeover of the gas atmosphere), further holding times, transfers of the catalyst intermediate to different apparatus, or interruptions to the calcining operation as a whole.

Since the catalyst precursor generally has a temperature of <100° C. before the commencement of calcination, it must normally be heated prior to step (i). Heating can be carried out using different gas atmospheres. Heating is preferably conducted in an oxidizing atmosphere, as defined under step (i), or in an inert gas atmosphere, as defined under step (iii). A change in gas atmosphere during the heating phase is also possible. Particular preference is given to heating in the oxidizing atmosphere which is also employed in step (i).

The invention further provides a catalyst for preparing maleic anhydride by heterogeneously catalyzed gas-phase oxidation of a hydrocarbon having at least four carbon atoms, said catalyst being obtainable by the process of the invention described above.

The catalyst which is preferably prepared by the process of the invention features a phosphorus/vanadium atomic ratio of from 0.9 to 1.5, with particular preference from 0.9 to 1.2, and with very particular preference from 1.0 to 1.1, an average oxidation state of the vanadium of from +3.9 to +4.4 and with particular preference from 4.0 to 4.3, a BET surface area of from 10 to 50 m$^2$/g and with particular preference from 20 to 40 m$^2$/g, a pore volume of from 0.1 to 0.5 ml/g and with particular preference from 0.2 to 0.4 ml/g, and a bulk density of from 0.5 to 1.5 kg/l and with particular preference from 0.5 to 1.0 kg/l.

The catalyst of the invention can be prepared industrially easily, quickly, and efficiently and, in the heterogeneously catalyzed gas-phase oxidation of a hydrocarbon having at least four carbon atoms to maleic anhydride, permits a high hydrocarbon velocity in combination with a high conversion, high activity, high selectivity, and a high space-time yield.

The invention additionally provides a process for preparing maleic anhydride by heterogeneously catalyzed gas-phase oxidation of a hydrocarbon having at least four carbon atoms with oxygenous gases which comprises using a catalyst of the invention as described above.

The process of the invention for preparing maleic anhydride generally makes use of shell-and-tube reactors. Suitable hydrocarbons are generally aliphatic and aromatic, saturated and unsaturated hydrocarbons having at least four carbon atoms, such as 1,3-butadiene, 1-butene, 2-cis-butene, 2-trans-butene, n-butane, $C_4$ mixture, 1,3-pentadiene, 1,4-pentadiene, 1-pentene, 2-cis-pentene, 2-trans-pentene, n-pentane, cyclopentadiene, dicyclopentadiene, cyclopentene, cyclopentane, $C_5$ mixture, hexenes, hexanes, cyclohexane, and benzene, for example. It is preferred to use 1-butene, 2-cis-butene, 2-trans-butene, n-butane, benzene or mixtures thereof. Particular preference is given to using n-butane and liquids and gases containing n-butane. The n-butane used may originate, for example, from natural gas, from steam crackers or from FCC crackers.

The hydrocarbon is generally added under flow control, i.e., with continual feeding of a defined amount per unit time. The hydrocarbon may be metered in liquid or gaseous form. Preference is given to metering in liquid form with subsequent vaporization prior to entry into the shell-and-tube reactor.

Oxidants used are oxygenous gases, such as air, synthetic air, oxygen-enriched gas, or else what is termed "pure" oxygen, i.e., oxygen originating, for example, from the fractionation of air. The oxygenous gas is also added under flow control.

The gas to be passed through the shell-and-tube reactor generally contains a hydrocarbon concentration of from 0.5 to 15% by volume and an oxygen concentration of from 8 to 25% by volume. The remaining fraction is composed of further gases such as nitrogen, noble gases, carbon monoxide, carbon dioxide, steam, oxygenated hydrocarbons (e.g., methanol, formaldehyde, formic acid, ethanol, acetaldehyde, acetic acid, propanol, propionaldehyde, propionic acid, acrolein, and crotonaldehyde), for example, and mixtures thereof. As a proportion of the total amount of hydrocarbon, the n-butane fraction is preferably $\geq 90\%$ and with particular preference $\geq 95\%$.

In order to ensure a long catalyst life and to further conversion, selectivity, yield, space velocity over the catalyst, and space-time yield, in the process of the invention it is preferred to feed a volatile phosphorus compound into the gas. The concentration of this compound at the beginning, i.e., at the reactor entry, is at least 0.2 ppm by volume, i.e., $0.2 \cdot 10^{-6}$ part by volume of the volatile phosphorus compound relative to the total volume of the gas at the reactor entry. Preference is given to an amount of from 0.2 to 20 ppm by volume, with particular preference from 0.5 to 10 ppm by volume. Volatile phosphorus compounds are all phosphorus compounds which are present in gaseous form at the desired concentration under the conditions in which they are employed. examples of suitable volatile phosphorus compounds include phosphines and phosphates. The $C_1$ to $C_4$ alkyl phosphates are particularly preferred, with very particular preference being given to trimethyl phosphate, triethyl phosphate, and tripropyl phosphate, especially triethyl phosphate.

The process of the invention is generally conducted at a temperature from 350 to 480° C. By this temperature is meant the temperature of the catalyst bed in the shell-and-tube reactor which said catalyst bed would have were the process to be practiced in the absence of a chemical reaction. If this temperature is not exactly the same at all points, the term refers to the numerical average of the temperatures along the reaction zone. This means in particular that the true temperature on the catalyst may also lie outside the stated range, owing to the exothermic nature of the oxidation reaction. The process of the invention is conducted preferably at a temperature of from 380 to 460° C., with particular preference from 380 to 430° C.

The process of the invention may be performed at a pressure below atmospheric pressure (e.g., up to 0.05 MPa abs) or else above atmospheric pressure (e.g., up to 10 MPa abs). The pressure referred to is the pressure prevailing within the shell-and-tube reactor unit. Preference is given to a pressure of from 0.1 to 1.0 MPa abs, with particular preference from 0.1 to 0.5 MPa abs.

The process of the invention can be implemented in two preferred modes, the straight pass mode and the recirculation mode. In the straight pass mode, maleic anhydride and any oxygenated hydrocarbon byproducts are removed from the reactor discharge and the remaining gas mixture is separated off and utilized where appropriate for heat generation. With the recirculation mode, maleic anhydride and any oxygenated hydrocarbon byproducts are again removed from the reactor discharge but some or all of the remaining gas mixture, which contains unreacted hydrocarbon, is recycled to the reactor. A further variant of the recirculation mode involves the removal of the unreacted hydrocarbon and its recycling to the reactor.

In one particularly preferred embodiment for the preparation of maleic anhydride, the starting hydrocarbon used is n-butane and the heterogeneously catalyzed gas-phase oxidation is conducted with a straight pass over the catalyst of the invention.

The process of the invention using the catalysts of the invention permits a high hydrocarbon space velocity over the catalyst in combination with high conversion as a result of high activity. The process of the invention further permits high selectivity, high yield, and hence also a high space-time yield of maleic anhydride.

DEFINITIONS

The variables used in this text, unless otherwise mentioned, are defined as follows:

$$\text{Space-time yield} = \frac{m_{\text{maleic anhydride}}}{V_{\text{catalyst}} \cdot t}$$

$$\text{Space velocity} = \frac{V_{\text{hydrocarbon}}}{V_{\text{catalyst}} \cdot t}$$

$$\text{Conversion } U = \frac{n_{\text{HC,reactor,in}} - n_{\text{HC,reactor,out}}}{n_{\text{HC,reactor,in}}}$$

$$\text{Selectivity } S = \frac{n_{\text{MAN,reactor,out}}}{n_{\text{HC,reactor,in}} - n_{\text{HC,reactor,out}}}$$

$$\text{Yield } A = U \cdot S$$

| | |
|---|---|
| $m_{\text{maleic anhydride}}$ | Mass of maleic anhydride produced [g] |
| $V_{\text{catalyst}}$ | Bulk volume of catalyst summated over all reaction zones [L] |
| $t$ | Time unit [h] |
| $V_{\text{hydrocarbon}}$ | Volume of the hydrocarbon in the gas phase, standardized to 0° C. and 0.1013 MPa, [L (stp)] (Arithmetic variable. Where a hydrocarbon is in the liquid phase under these conditions, the hypothetical gas volume is calculated from the ideal gas law.) |
| $U$ | Conversion of hydrocarbons per reactor pass |
| $S$ | Selectivity from maleic anhydride per reactor pass |
| $A$ | Yield of maleic anhydride per reactor pass |
| $n_{\text{HC,reactor,in}}$ | Volume flow of hydrocarbons at the reactor entry [mol/h] |
| $n_{\text{HC,reactor,out}}$ | Volume flow of hydrocarbons at the reactor exit [mol/h] |
| $n_{\text{HC,plant,in}}$ | Volume flow of hydrocarbons at the plant entry [mol/h] |
| $n_{\text{HC,plant,out}}$ | Volume flow of hydrocarbons at the plant exit [mol/h] |
| $n_{\text{MAN,reactor,in}}$ | Volume flow of maleic anhydride at the reactor exit [mol/h] |
| $n_{\text{MAN,plant,out}}$ | Volume flow of maleic anhydride at the plant exit [mol/h] |

EXAMPLES

Determination of the Filtration Time (for Examples 1 to 4)

The filtration time was determined by introducing the suspension obtained in examples 1 to 4 at temperature T into a glass suction filter, leaving it there without further mechanical intervention, such as stirring, for example, and monitoring the progress of the filtration. The filtration time is defined as the interval between the application of the suspension to the glass suction filter and the time when there was no supernatant mother liquor above the filtercake.

Determination of the Stirring Power

The stirring power was determined in accordance with the remarks in the description relating to calculation of the modified dimensionless Reynolds number, $Re_M$, by formula (VI), determination of the dimensionless performance coefficient $N_e$, which results from the Reynolds number and takes into account the form of stirrer, and calculation in accordance with formula (V). The determination of the stirring power was based on the rotational speed of the stirrer, n, the stirrer diameter d, the kinematic viscosity ν of the mixed reactants prior to reaction at 20° C., the density ρ of the mixed ingredients prior to reaction at 20° C., and the diagram relating to determination of the performance characteristic in accordance with Marko Zlokarnik, "Rührtechnik—Theorie und Praxis", Springer-Verlag Berlin 1999, page 77, FIG. 2.2.

Determination of the Filtration Resistance by Pressure Filtration

Determining the filtration resistance by pressure filtration is a known method and is described, for example, in VDI Guideline 2762 "Filterability of suspensions/determination of the filtercake resistance", VDI, February 1997. For experimental determination of the filtration resistance, the amounts of suspension indicated in the individual examples were applied to a heatable pressure suction filter at the desired filtration temperature. This suction filter was equipped with a polypropylene weave having a filter area A of 20 cm$^2$, a maximum pore diameter of 45 μm, and an average pore diameter of 10 μm (fabric "PP 2703" from Verseidag). The pressure suction filter was then sealed and the desired differential pressure Δp of 0.4 MPa was set by injecting nitrogen and was kept constant throughout the pressure filtration. When the bottom drain tap was opened, recording of the time began. The purpose of the filtrate mass over time was registered by a computer. Toward the end of the filtration, cracks formed which led to a rapid evening-out of the pressure difference. This point in time was taken as the end point, $t_{end}$, for the measurement of the filtration time. After the end of the pressure filtration, the total filtrate volume $V_{F,end}$ and the filtercake height $H_{end}$ were measured. The filtration resistance $\alpha^*_H \eta$ was then calculated from the data found in accordance with the simplified formula $$\alpha^*_H \eta = \frac{2 \cdot \Delta p \cdot t_{end} \cdot A}{H_{end} \cdot V_{F,end}}$$

disregarding the very much smaller filter resistance $R_T$ of the polypropylene weave.

Determination of the Particle Size Distribution

The particle size distribution was determined by introducing a representative sample, containing a solids content of approximately 1 g, of each of the suspensions obtained in examples 5.1 to 5.3 into a glass beaker and making up the level to 100 mL with isobutanol. The suspension, homogenized by intensive stirring, was then passed continuously through the measuring cell of a laser diffraction spectrometer (model: Malvern Mastersizer S) and subjected to measurement with a gas laser of wavelength 632.8 nm. The beam of light emerging from the sample was imaged by a lens system onto a detector, with the undiffracted light being screened out. The local intensities at the detector elements were read into a computer and converted to a particle size distribution. The graph shows the volume fraction of the suspension with particles smaller than or equal to the particle size indicated on the abscissa.

Determination of the Residual Isobutanol Content of the Dried Catalyst Precursor The residual isobutanol content was determined by weighing a precise amount in the region of 4 g of the dried catalyst precursor and a precise amount of about 10 g of N,N-dimethylformamide into a heatable stirred apparatus equipped with reflux condenser. The contents were then heated to boiling temperature with stirring and were left under these conditions for 30 minutes. After cooling, the suspension was filtered and the isobutanol content of the filtrate was quantified by gas chromatography. The residual isobutanol content was then calculated from the isobutanol concentration found in the N,N-dimethylformamide and from the initial weighings of N,N-dimethylformamide and catalyst precursor.

Experimental Plant

The experimental plant was equipped with a feed unit and a reactor tube. Replacing a shell-and-tube reactor by a reactor tube is entirely valid on the laboratory or pilot plant scale provided the dimensions of the reactor tube are within the region of an industrial reactor tube. The plant was operated in straight pass mode.

The hydrocarbon was added in liquid form under flow control via a pump. Air was added under flow control as the oxygenous gas. Triethyl phosphate (TEP) was added in liquid form, in solution in water, again under flow control.

The shell-and-tube reactor unit comprised a shell-and-tube reactor having one reactor tube. The length of the reactor tube was 6.5 m and its internal diameter was 22.3 mm. Within the reactor tube, a tube with an external diameter of 6 mm protected a multiple thermocouple having 20 temperature measurement points. The reactor tube was surrounded by a thermostatable circuit of heat transfer medium and was traversed from top to bottom by the reaction gas mixture. The upper 0.3 m of the reactor tube was filled with an inert material and constituted the preheating zone. The reaction zone contained in each case 2.2 L of catalyst. The heat transfer medium used was a salt melt.

Directly downstream of the shell-and-tube reactor unit, gaseous product was taken off and passed to a gas chromatograph for online analysis. The main stream of the gaseous reactor discharge was removed from the plant.

The plant was operated as follows:

n-Butane concentration at reactor entry=2.0% by volume

WHSV=2000 L(stp)/$L_{catalyst}$·h

Pressure at the reactor exit=0.2 MPa abs

Concentration of triethyl phosphate (TEP)=2 ppm by volume

Concentration of steam=1.5% by volume

Example 1

Effect of the average heating rate following the addition of phosphoric acid to the initial charge of vanadium pentoxide and isobutanol at 25° C. on the filtration time The stirred apparatus was equipped with a jacket vessel, thermostated by way of ethylene glycol, a reflux condenser, a temperature sensor, a stirrer, and four uniformly arranged flow disrupters. The height of the flow disrupters corresponded to the internal height of the jacket vessel and protruded into the vessel to the extent of 10% of the internal diameter of the jacket vessel. This apparatus was charged at 25° C. with 242.6 g of vanadium pentoxide and 286.3 g of 105% strength phosphoric acid in 2 L of isobutanol and was heated to the boiling temperature of the reaction mixture (approximately 108° C.) at the desired average heating rate with continuous stirring and under reflux. After the boiling temperature had been reached, the reaction mixture was held at this temperature for 16 hours. Throughout this time, the suspension was stirred with a constant stirring power, in other words at constant rotational speed. It was then cooled to 85° C., still with stirring, filtered through a glass suction filter (porosity 4, diameter 19 cm with a filter area of 284 cm$^2$) at 85° C., and the filtration time was measured. The results obtained are reproduced in table 1.

As is evident from comparing examples 1.1 and 1.2, the heating rate following the addition of the phosphoric acid to the initial charge of vanadium pentoxide and isobutanol has a decisive effect on the filtration time. When a heating rate of 2° C./min is set, the filtration time under otherwise identical conditions is shorter by a factor of 4.7 than is the case when a heating rate of 1° C./min is set.

Example 2

Effect of the stirring power during the reaction of the vanadium pentoxide in the presence of isobutanol with phosphoric acid on the filtration time A stirred apparatus as described in example 1 was charged at 25° C. with 242.6 g of vanadium pentoxide and 286.3 g of 105% strength phosphoric acid in 2 L of isobutanol and this initial charge was heated to the boiling temperature of the reaction mixture (about 108° C.) at an average heating rate of 2° C./min with continuous stirring and under reflux. When the boiling temperature had been reached, the reaction mixture was held at this temperature for 16 hours. Throughout this time the suspension was stirred at constant stirring power, in other words at a constant rotational speed. It was then cooled to 85° C., still with stirring, and filtered through a glass suction filter (porosity 4, diameter 19 cm with a filter area of 284 $cm^2$) at 85° C., and the filtration time was measured. The results obtained are reproduced in table 2.

Examples 2.1 to 2.3 show that with decreasing stirring power, which at the same stirrer geometry was adjusted by lowering the rotational speed of the stirrer, there was a significant shortening in the filtration time. Thus with a reduction in the stirring power from 0.61 W/kg (example 2.1) to 0.09 W/kg (example 2.3) the filtration time was shortened by a factor of 3.1.

Examples 2.3 and 2.4 show that the effect described is substantially independent of the stirrer geometry. When a very similar stirring power of 0.09 and 0.07 W/kg, respectively, is set, the primarily radially mixing impeller stirrer and the primarily axially mixing propeller stirrer gave the same filtration time under otherwise identical conditions.

Example 3

Effect of the Filtration Temperature on the Filtration Time

A stirred apparatus as described in example 1 was charged at 25° C. with 242.6 g of vanadium pentoxide and 286.3 g of 105% strength phosphoric acid in 2 L of isobutanol and this initial charge was heated to the boiling temperature of the reaction mixture (about 108° C.) at an average heating rate of 2° C./min with continuous stirring and under reflux. When the boiling temperature had been reached, the reaction mixture was held at this temperature for 16 hours. Throughout this time the suspension was stirred at constant stirring power, in other words at a constant rotational speed. It was then cooled to the desired filtration temperature, still with stirring, and filtered through a glass suction filter (porosity 4, diameter 13 cm with a filter area of 133 $cm^2$) at the desired filtration temperature, and the filtration time was measured. The results obtained are reproduced in table 3.

Comparing example 3.1 with 3.2 and example 3.3 with 3.4 shows that at a filtration temperature of 85° C. as against a filtration temperature of 25° C. the filtration time achieved is shorter by a factor of 2.3. This effect occurs irrespective of the nature of the stirrer used and irrespective of the stirring power employed.

Example 4

Effect of the Addition Temperature of the Phosphoric Acid and of the Vanadium pentoxide on the Filtration Time In example 4.1, a stirred apparatus as described in example 1 was charged at 25° C. with 242.6 g of vanadium pentoxide and 286.3 g of 105% strength phosphoric acid in 2 L of isobutanol and this initial charge was heated to the boiling temperature of the reaction mixture (about 108° C.) at an average heating rate of 1° C./min with continuous stirring and under reflux. When the boiling temperature had been reached, the reaction mixture was held at this temperature for 16 hours. Throughout this time, the suspension was stirred at constant stirring power, in other words at constant rotational speed. Subsequently it was cooled to 85° C., still with stirring, and was filtered through a glass suction filter (porosity 4, diameter 19 cm with a filter area of 284 $cm^2$) at 85° C., and the filtration time was measured.

In example 4.2, a stirred apparatus as described in example 1 was charged at 25° C. with 242.6 g of vanadium pentoxide in 2 L of isobutanol and this initial charge was heated to 92° C. at an average heating rate of 1° C./min with continuous stirring and under reflux. At this temperature, 286.3 g of 105% strength phosphoric acid conditioned at 25° C. were added. The reaction mixture was then heated to its boiling temperature (about 108° C.) and held at this temperature for 16 hours. Throughout this time, the suspension was stirred at constant stirring power, in other words at constant rotational speed. Subsequently it was cooled to 85° C., still with stirring, and was filtered through a glass suction filter (porosity 4, diameter 19 cm with a filter area of 284 $cm^2$) at 85° C., and the filtration time was measured.

In example 4.3, in a stirred apparatus as described in example 1, 1.8 L of isobutanol were heated to 92° C. with continuous stirring and under reflux and, at this temperature, 242.6 g of vanadium pentoxide powder conditioned at 25° C. and a solution of 286.3 g of 105% strength phosphoric acid in 0.2 L of isobutanol, likewise conditioned at 25° C., were fed in over a period of 30 minutes. The reaction mixture was then heated to its boiling temperature (about 108° C.) and held at this temperature for 16 hours. Throughout this time, the suspension was stirred at constant stirring power, in other words at constant rotational speed. Subsequently it was cooled to 85° C., still with stirring, and was filtered through a glass suction filter (porosity 4, diameter 19 cm with a filter area of 284 $cm^2$) at 85° C., and the filtration time was measured.

The results obtained are reproduced in table 4.

Comparing example 4.1 with 4.2 shows that the addition of the phosphoric acid to the initial charge of vanadium pentoxide and isobutanol at a temperature of 92° C. achieves a filtration time which is shorter by a factor of 2 than when the addition takes place at 25° C. Where both vanadium pentoxide and phosphoric acid are added at 92° C. to isobutanol, the resulting filtration time is shorter by a factor of 3 than in the case of the addition at 25° C.

Example 5

Effect of the average heating rate following the addition of the phosphoric acid to the initial charge of vanadium pentoxide and isobutanol at 25° C. and the stirring power during the reaction on the filtration time and on the particle size distribution.

A stirred apparatus as described in example 1 was charged at 25° C. with 242.6 g of vanadium pentoxide and 286.3 g of 105% strength phosphoric acid in 2 L of isobutanol and this initial charge was heated at an average heating rate of 1° C./min (example 5.1) or 2° C./min (examples 5.2 and 5.3) to the boiling temperature of the reaction mixture (about 108° C.) with continuous stirring and under reflux. When the boiling temperature had been reached, the reaction mixture was held at this temperature for 16 hours. Throughout this time, the suspension was stirred at constant stirring power, in other words at constant rotational speed, namely 0.19 W/kg suspension in examples 5.1 and 5.2 and 0.07 W/kg suspension in example 5.3. Thereafter, still with stirring, the suspension was cooled to the desired filtration temperature of 25° C. and a pressure filtration was carried out in order to determine the filtration resistance.

The particle size distribution was determined by taking 100 mL of a representative sample of the suspension from the stirred apparatus after cooling and subjecting it to measurement as described under "determination of the particle size distribution".

The results obtained are reproduced in table 5. A graph of the volume fraction of the suspension with particles less than or equal to the particle size indicated on the abscissa is given in FIG. 1.

Comparing example 5.1 with 5.2 shows the significant effect of the heating rate following addition of the phosphoric acid to the initial charge of vanadium pentoxide and isobutanol at 25° C. At a lower heating rate of 1° C./min a relatively high filtration resistance of $99 \cdot 10^{13}$ mPa·s/m², a filtration time of 115 minutes, and a volume fraction of the suspension with particles $\leq 10$ μm of 25% are obtained. On doubling the heating rate to 2° C./min (example 5.2) a relatively low filtration resistance of $13 \cdot 10^{13}$ mPa·s/m², a filtration time of 14 minutes, and a volume fraction of the suspension with particles $\leq 10$ μm of 17% are obtained. Since example 5.1 makes use of only one of the three inventive measures, namely the setting of a stirring power of 0.19 W/kg suspension, this example constitutes a comparative example.

When the stirring power is lowered relative to that of example 5.2 to 0.07 W/kg suspension (example 5.3), the filtration resistance is only $5.7 \cdot 10^{13}$ mPa·s/m², the filtration time is 7 minutes, and the volume fraction of the suspension with particles $\leq 10$ μm is 5%.

Example 6

Preparation of the Catalyst Precursor on the Metric Ton Scale

For preparing the catalyst precursor on the metric ton scale a plant as described below was used. The precipitation vessel employed was a steel/enamel stirred tank having a three-stage impeller stirrer and a capacity of 8 m³, and was externally heated with pressurized water. The precipitation vessel was equipped with a dip pipe (diameter 70 mm) and a flow breaker paddle (diameter 180 mm) as flow disrupter. To ensure operation under reflux, a water-cooled condenser was mounted above the stirred tank, connected by way of a feed line and a drain line. Isobutanol and phosphoric acid were metered via a pump and vanadium pentoxide via a conveying screw. At the bottom of the stirred tank there was a valve whose purpose was to transfer the suspension, after the end of the reaction, via a line to a heatable pressure suction filter. This filter was fitted with a woven Hasteloy mesh with a mesh size of approximately 20 μm and had a diameter of 2.7 m, corresponding to a filter area of just under 6 m². The pressure suction filter was heated by way of the outer wall and an internally mounted stirrer. The stirrer is mounted centrally, is adjustable in height, and was suitable variously for stirring up the suspension, for smoothing out the filtercake, for introducing heat during the drying operation, and for loosening during product discharge. The mother liquor passing through the filter mesh was collected in a collection vessel. In order to allow pressure filtration, nitrogen could be injected in the section above the filter mesh. In order to allow drying under reduced pressure, the pressure suction filter was further provided with a vacuum connection.

For the preparation of the catalyst precursor on the metric ton scale in accordance with example 6, the stirred tank was rendered inert with nitrogen and charged with 6.1 m³ of isobutanol. Following startup of the three-stage impeller stirrer, which throughout the precipitation operation was regulated at a stirring power of 0.68 W/kg, 736 kg of vanadium pentoxide were fed in via the conveying screw and 900 kg of 105% strength phosphoric acid were pumped in at room temperature (20–30° C.). The pump was cleaned by passing a further 0.2 m³ of isobutanol through it. The reaction mixture was subsequently heated under reflux to about 100 to 108° C. at a heating rate of 1° C./min and was left under these conditions for 14 hours. Thereafter, 5 L of a representative sample of the suspension were taken for the purpose of determining the filtration resistance and the remaining, hot suspension was drained off into the pressure suction filter, which had been rendered inert with nitrogen beforehand and heated to about 144° C. with 0.4 MPa (4 bar) steam. The stirrer of the pressure suction filter was operated a 3 rpm in order to ensure uniform formation of the filtration base layer when the suspension is introduced. After the stirred tank had been fully discharged, it was rinsed with 0.2 m³ of isobutanol in order to remove residues of product which were still adhering. When all of the product suspension was on the pressure suction filter, the steam-heated stirrer was removed from the suspension and the steam heating was set to a temperature of about 100° C. This prevented boiling of the isobutanol. The section above the filter mesh was then injected, beginning at 0.1 MPa abs, with nitrogen to a pressure of 0.35 MPa abs, and, at the same time as the application of pressure was begun, the drain tap below the. filter was opened. The beginning of the application of pressure was accompanied by commencement of the measurement of the filtration time. Toward the end of pressure filtration, the mother liquor over the filtercake fell and initial cracks were formed, leading to a rapid drop in pressure. The rapid drop in pressure was taken as the end point for the measurement of the filtration time. On reaching the drop in pressure, the stirrer for smoothing out the filtercake was withdrawn far enough to allow pressure to build up again. By continuous introduction of nitrogen and stirring with the stirrer heated to 100° C., the filtercake was blown dry within a period of about one hour. No further increase in the fill level in the collection vessel was then observed. After the filtercake had been blown dry, the steam heating of the stirrer was set at 0.55 MPa (5.5 bar), corresponding to a temperature of approximately 155° C., and at the same time reduced pressure was applied, namely a pressure in the range from 0.1 MPa abs (1 bar abs) to 15 kPa abs (150 mbar abs). Further stirring in the region of the filtercake to be dried ensured uniform introduction of heat. Drying was carried out to a residual isobutanol content of <2% by weight in the dried catalyst precursor. The filtration time was 120 hours.

The results obtained are reproduced in table 6.

Example 7

Preparation of the Catalyst Precursor on the Metric Ton Scale

The catalyst precursor was prepared in the plant described in example 6. The stirred tank, rendered inert with nitrogen, was charged with 6.1 m³ of isobutanol. Following startup of the three-stage impeller stirrer, which throughout the precipitation operation was regulated at a stirring power of 0.25 W/kg, 736 kg of vanadium pentoxide were fed in via the conveying screw at room temperature (20–30° C.). The mixture was subsequently heated to 90° C. under reflux at a heating rate of 1° C./min. Then, at this temperature, 900 kg of 105% strength phosphoric acid were pumped in. The pump was cleaned by passing a further 0.2 m³ of isobutanol through it. The reaction mixture was subsequently heated to about 100 to 108° C. under reflux and the subsequent procedure was as described in example 6. Drying was carried out to a residual isobutanol content of <2% by weight in the dried catalyst precursor. The results obtained are reproduced in table 6. The filtration time was 2.7 hours.

Example 8

Preparation of the Catalyst Precursor on the Metric Ton Scale

The catalyst precursor was prepared in the plant described in example 6. The stirred tank, rendered inert with nitrogen, was charged with 6.1 m³ of isobutanol. Following startup of the three-stage impeller stirrer, which throughout the precipitation operation was regulated at a stirring power of 0.25 W/kg, the isobutanol was heated to 90° C. under reflux. Then, at this temperature, the addition of 736 kg of vanadium pentoxide by way of the conveying screw was commenced. When, after about 20 minutes, approximately ⅔ of the desired amount of vanadium pentoxide had been added, the pump introduction of 900 kg of 105% strength phosphoric acid was commenced, still accompanied by the addition of vanadium pentoxide. The pump was cleaned by passing a further 0.2 m³ of isobutanol through it. The reaction mixture was subsequently heated to about 100 to 108° C. under reflux and the subsequent procedure was as described in example 6. Drying was carried out to a residual isobutanol content of <2% by weight in the dried catalyst precursor. The filtration time was 1.7 hours.

The results obtained are reproduced in table 6.

Examples 6 to 8 on preparing the catalyst precursor on the metric ton scale showed the effects of the various measures on the filtration time and/or the filtration resistance. In example 6, in which the stirring power was 0.68 W/kg suspension, the temperature at which the vanadium pentoxide and the phosphoric acid were added was from 20 to 30° C., the heating rate following addition of the phosphoric acid was 1° C./min, and the filtration temperature was from 80 to 100° C., it was possible to achieve a filtration resistance of $70 \cdot 10^{13}$ mPa·s/m² and a filtration time of 120 hours. Since example 6 makes use of only one of the three inventive measures, namely that of filtering at a temperature from 80 to 100° C., that example is a comparative example.

Where—as in example 7—the stirring power is lowered to 0.25 W/kg suspension and the phosphoric acid is added to the vanadium pentoxide/isobutanol suspension conditioned at 90° C., the filtration time falls significantly to 2.7 hours. Where, in addition, the vanadium pentoxide is added to isobutanol conditioned at 90° C., the filtration time falls to 1.7 hours and the filtration resistance to $1.3 \cdot 10^{13}$ mPa·s/m².

Example 9

Catalytic Test of the Catalyst from Example 8

Precursor powder prepared in accordance with example 8 was conditioned for 2 hours in air in a rotary tube having a length of 6.5 m and an internal diameter of 0.9 m and containing spiral coils. The rotational speed of the rotary tube was 0.4 rpm. The powder was conveyed into the rotary tube at a rate of 60 kg/h. The air supply was 100 m³/h. The temperatures of the five heating zones (which were of equal length), measured directly on the outside of the rotary tube, were 250° C., 300° C., 340° C., 340° C., and 340° C. After cooling to room temperature, the VPO precursor was intimately mixed with 1% by weight of graphite and the mixture was compacted in a roll compactor. The fines in the compacted material, with a particle size <400 μm, were sieved off and passed back for compacting. The coarse material, with a particle size ≧400 μm, was mixed with a further 2% by weight of graphite and the mixture was tableted in a tableting machine to give 5×3×2.5 mm hollow cylinders (external diameter×height×inner-hole diameter). In order to obtain the desired amount of approximately 3 t of catalyst precursor, a number of runs were carried out in example 8.

Approximately 2.7 t of the resulting 5×3×2.5 mm hollow cylinders (see "preparation of the catalyst precursor") were applied continuously in a bed height of from 9 to 10 cm to the gas-permeable conveying belt of a belt calcining means comprising two identical belt calcining kilns in series, with a total of eight calcining zones. The first 1.4 t were used for the one-off setting of the operating parameters of the belt calcining means. Since they did not constitute a uniform material, they have not been considered any further in the text below.

The belt calcining means was operated at atmospheric pressure. Between zones 4 and 5 there was an encapsulated transition zone. Each of the eight calcining zones included a fan, in order to generate a gas circulation. Each of the eight calcining zones was supplied with the desired amount of desired fresh gas. To maintain the desired atmospheric pressure, an appropriate amount of gas was taken off. The volume of gas circulating in each calcining zone per unit time was greater than the volume of the gas supplied or taken off per unit time. In order to reduce the level of gas exchange, there was a partition wall between each pair of successive calcining zones, which was open in the region of the flow of the catalyst precursor. The length of each calcining zone, $l_n$, was 1.45 m. The speed of the conveyor belt was set in accordance with the desired residence time of approximately 2 hours per calcining zone. The individual zones were operated as shown in Table 7:

TABLE 7

Parameters for the operation of the belt calcining means

| Zone | Temperature | Fresh gas supplied |
|---|---|---|
| Calcining zone 1 | Heating to 250° C. | Air |
| Calcining zone 2 | Holding at 250° C. | Air |
| Calcining zone 3 | Holding at 250° C. | Air |
| Calcining zone 4 | Heating to 310° C. | Air |
| Transition zone | Cooling to 200° C. | Air |
| Calcining zone 5 | Heating to 425° C. | $N_2$ |
| Calcining zone 6 | Holding at 425° C. | $N_2/H_2O$ steam (1:1) |
| Calcining zone 7 | Holding at 425° C. | $N_2/H_2O$ steam (1:1) |
| Calcining zone 8 | Cooling to room temperature | $N_2$ |

Using a representatively selected individual sample of 2.2 L of the continuously calcined catalyst, a catalytic performance test was carried out in the experimental plant described above. With a salt bath temperature of 395° C., and a n-butane conversion of 84.8% was achieved. The yield of maleic anhydride was 57.5%.

TABLE 1

Effect of the average heating rate following addition of phosphoric acid to the initial charge of vanadium pentoxide and isobutanol at 25° C. on the filtration time

| | Example | |
|---|---|---|
| | 1.1 | 1.2 |
| Stirrer geometry | Impeller (single-stage) | Impeller (single stage) |
| Stirrer diameter [m] | 0.0855 | 0.0855 |
| Stirrer speed [rpm] | 440 | 440 |
| Modified Reynolds number $Re_M$ | 5155 | 5155 |
| Performance coefficient $N_e$ | 0.75 | 0.75 |
| Stirring power [W/kg] | 0.61 | 0.61 |
| Addition temperature of $V_2O_5$ [° C.] | 25 | 25 |
| Addition temperature of phosphoric acid [° C.] | 25 | 25 |
| Heating rate [° C./min] | 2 | 1 |
| Filtration temperature [° C.] | 85 | 85 |
| Filtration time [min] | 5.5 | 26 |

Kinematic viscosity V of the mixed reactants at $10.4 \cdot 10^{-6}$ m²/s 20° C.:

Density ρ of the mixed reactants at 20° C.: 962 kg/m³

TABLE 2

Effect of stirring power during the reaction of the vanadium pentoxide in the presence of isobutanol with phosphoric acid on the filtration time

| | Example | | | |
|---|---|---|---|---|
| | 2.1 | 2.2 | 2.3 | 2.4 |
| Stirrer geometry | Impeller (single-stage) | Impeller (single-stage) | Impeller (single-stage) | Propeller (single-stage) |
| Stirrer diameter [m] | 0.0855 | 0.0855 | 0.0855 | 0.08 |
| Stirrer speed [rpm] | 440 | 300 | 230 | 300 |
| Modified Reynolds number $Re_M$ | 5155 | 3515 | 2694 | 3077 |
| Performance coefficient $N_e$ | 0.75 | 0.75 | 0.75 | 0.40 |
| Stirrer power [W/kg] | 0.61 | 0.19 | 0.09 | 0.07 |
| Addition temperature of $V_2O_5$ [° C.] | 25 | 25 | 25 | 25 |
| Addition temperature of phosphoric acid [° C.] | 25 | 25 | 25 | 25 |
| Heating rate [° C./min] | 2 | 2 | 2 | 2 |
| Filtration temperature [° C.] | 85 | 85 | 85 | 85 |
| Filtration time [min] | 5.50 | 3.25 | 1.75 | 1.75 |

Kinematic viscosity V of the mixed reactants at 20° C.: $10.4 \cdot 10^{-6}$ m²/s
Density ρ of the mixed reactants at 20° C.: 962 kg/m³

TABLE 3

Effect of filtration temperature on the filtration time

| | Example | | | |
|---|---|---|---|---|
| | 3.1 | 3.2 | 3.3 | 3.4 |
| Stirrer geometry | Impeller (single-stage) | Impeller (single-stage) | Propeller (single-stage) | Propeller (single-stage) |
| Stirrer diameter [m] | 0.0855 | 0.0855 | 0.08 | 0.08 |
| Stirrer speed [rpm] | 300 | 300 | 300 | 300 |
| Modified Reynolds number $Re_M$ | 3515 | 3515 | 3077 | 3077 |
| Performance coefficient $N_e$ | 0.75 | 0.75 | 0.40 | 0.40 |
| Stirring power [W/kg] | 0.19 | 0.19 | 0.07 | 0.07 |
| Addition temperature of $V_2O_5$ [° C.] | 25 | 25 | 25 | 25 |
| Addition temperature of phosphoric acid [° C.] | 25 | 25 | 25 | 25 |
| Heating rate [° C./min] | 2 | 2 | 2 | 2 |
| Filtration temperature [° C.] | 25 | 85 | 25 | 85 |
| Filtration time [min] | 51 | 22 | 14 | 6 |

Kinematic viscosity V of the mixed reactants at 20° C.: $10.4 \cdot 10^{-6}$ m²/s
Density ρ of the mixed reactants at 20° C.: 962 kg/m³

TABLE 4

Effect of the addition temperature of the phosphoric acid and of the vanadium pentoxide on the filtration time

| | Example | | |
|---|---|---|---|
| | 4.1 | 4.2 | 4.3 |
| Stirrer geometry | Impeller (single-stage) | Impeller (single-stage) | Impeller (single-stage) |
| Stirrer diameter [m] | 0.0855 | 0.0855 | 0.0855 |
| Stirrer speed [rpm] | 350 | 350 | 350 |
| Modified Reynolds number $Re_M$ | 4100 | 4100 | 4100 |
| Performance coefficient $N_e$ | 0.75 | 0.75 | 0.75 |
| Stirring power [W/kg] | 0.31 | 0.31 | 0.31 |
| Addition temperature of $V_2O_5$ [° C.] | 25 | 25 | 92 |
| Addition temperature of phosphoric acid [° C.] | 25 | 92 | 92 |
| Heating rate [° C./min]* | | 1 | |
| Filtration temperature [° C.] | 85 | 85 | 85 |
| Filtration time [min] | 6 | 3 | 2 |

*following the addition of the phosphoric acid.
Kinematic viscosity V of the mixed reactants at 20° C.: $10.4 \cdot 10^{-6}$ m²/s
Density ρ of the mixed reactants at 20° C.: 962 kg/m³

TABLE 5

Effect of the average heating rate following the addition of the phosphoric acid to the initial charge of vanadium pentoxide and isobutanol at 25° C. and of the stirring power during the reaction on the filtration time and on the particle size distribution

|  | Example | | |
|---|---|---|---|
|  | 5.1* | 5.2 | 5.3 |
| Stirrer geometry | Impeller (single-stage) | Impeller (single-stage) | Propeller (single-stage) |
| Stirrer diameter [m] | 0.0855 | 0.0855 | 0.08 |
| Stirrer speed [rpm] | 300 | 300 | 300 |
| Modified Reynolds number $Re_M$ | 3515 | 3515 | 3077 |
| Performance coefficient $N_e$ | 0.75 | 0.75 | 0.40 |
| Stirring power [W/kg] | 0.19 | 0.19 | 0.07 |
| Addition temperature of $V_2O_5$ [° C.] | 25 | 25 | 25 |
| Addition temperature of phosphoric acid [° C.] | 25 | 25 | 25 |
| Heating rate [° C./min] | 1 | 2 | 2 |
| Filtration temperature [° C.] | 25 | 25 | 25 |
| Filtration resistance [$10^{13}$ mPa·s/m²] | 99 | 13 | 5.7 |
| Filtration time [min] | 115 | 14 | 7 |
| Volume fraction of the suspension with particles ≦ 10 μm | 25 | 17 | 5 |

*comparative example
Kinematic viscosity V of the mixed reactants at 20° C.: $10.4 \cdot 10^{-6}$ m²/s
Density ρ of the mixed reactants at 20° C.: 962 kg/m³

TABLE 6

Preparation of the catalyst precursor on the metric ton scale

|  | Example | | |
|---|---|---|---|
|  | 6* | 7 | 8 |
| Stirrer geometry | Impeller (three-stage) | Impeller (three-stage) | Impeller (three-stage) |
| Stirrer diameter [m] | 1.09 | 1.09 | 1.09 |
| Stirrer speed [rpm] | 95 | 68 | 68 |
| Modified Reynolds number $Re_M$ | $1.81 \cdot 10^5$ | $1.29 \cdot 10^5$ | $1.29 \cdot 10^5$ |
| Performance coefficient $N_e$ | 0.75 | 0.75 | 0.75 |
| Stirring power [W/kg] | 0.68 | 0.25 | 0.25 |
| Addition temperature of $V_2O_5$ [° C.] | 15–30° C. | 15–30° C. | 90 |
| Addition temperature of phosphoric acid [° C.] | 15–30° C. | 90 | 90 |
| Heating rate [° C./min] | about 1 | about 1 | about 1 |
| Filtration temperature [° C.] | 80–100 | 80–100 | 80–100 |
| Filtration resistance [$10^{13}$ mPa·s/m²] | 70 | n.d. | 1.3 |
| Filtration time [h] | 120 | 2.7 | 1.7 |

*comparative example
n.d.: not determined.
Kinematic viscosity V of the mixed reactants at 20° C.: $10.4 \cdot 10^{-6}$ m²/s
Density ρ of the mixed reactants at 20° C.: 962 kg/m³

We claim:

1. A process for preparing a vanadium, phosphorus, and oxygen catalyst precursor for preparing maleic anhydride by heterogeneously catalyzed gas-phase oxidation of a hydrocarbon having at least four carbon atoms, by reacting vanadium pentoxide (I) in the presence of a primary or secondary, noncyclic or cyclic, unbranched or branched, saturated alcohol having from 3 to 6 carbon atoms (II) with from 102 to 110% by weight of phosphoric acid (III) in a temperature range from 80 to 160° C. with stirring and subsequently filtering the resultant suspension, which comprises using the following measure:

(a) adding the phosphoric acid (III) to the vanadium pentoxide (I), suspended in the alcohol (II) and heated to 60 to 160° C., the time of contact between the vanadium pentoxide (I) and the alcohol (II) prior to commencement of the addition of the phosphorus compound (III) at a temperature ≧50° C. being ≦1 hour; and at least one of the measures from the series (b) during the reaction of the vanadium pentoxide (I) in the presence of the alcohol (II) with the phosphoric acid (III), exposing the reaction mixture to a stirring power of from 0.01 to 0.6 W/kg suspension, the calculation of the stirring power being based on the physicochemical, properties of the mixed reactants prior to reaction and at 20° C.; and (c) filtering at a temperature of from 65° to 160° C.;
to set a filtration resistance $\alpha_H \cdot \eta$ of $\leq 25 \cdot 10^{13}$ mPa·s/m².

2. A process as claimed in claim 1, wherein in measure (a) the phosphoric acid (III) is added to the vanadium pentoxide (I), which has been suspended in the alcohol (II) and heated to 80 to 160° C.

3. A process as claimed in claim 1, wherein in measure (a) the vanadium pentoxide (I) heated to ≧50° C. is prepared by combining vanadium pentoxide (I) conditioned at ≧0° C. and <50° C. with the alcohol (II) conditioned at from 50 to 160° C.

4. A process as claimed in claim 1, wherein measure (b) involves exposure to a stirring power of from 0.01 to 0.5 W/kg suspension.

5. A process as claimed in claim 1, wherein for measure (c) a filtration temperature of from 80 to 160° C. is set.

6. A process as claimed in claim 1, wherein a filtration resistance copy of $\alpha_H \cdot \eta$ of $\leq 10 \cdot 10^{13}$ mPas/m2 is set.

7. A process as claimed in claim 1, wherein a suspension is prepared in which the fraction of particles ≦10 μm in size is ≦30%.

8. A process as claimed in claim 1, wherein a suspension is prepared in which the fraction of particles ≦10 μm in size is ≦20%.

9. A process as claimed in claim 1, wherein said alcohol (II) is isobutanol.

10. A process for preparing a vanadium-phosphorus-oxygen catalyst for preparing maleic anhydride by heterogeneously catalyzed gas-phase oxidation of a hydrocarbon having at least four carbon atoms, by treating a vanadium, phosphorus, and oxygen catalyst precursor in at least one atmosphere comprising oxygen ($O_2$), hydrogen oxide ($H_2O$) and/or inert gas in a temperature range from 200 to 600° C., which comprises using a catalyst precursor obtained by the process defined in claim 1.